(12) United States Patent
Doan et al.

(10) Patent No.: US 6,968,237 B2
(45) Date of Patent: Nov. 22, 2005

(54) IMPLANTABLE CORONARY SINUS LEAD AND LEAD SYSTEM

(75) Inventors: Phong D. Doan, Stevenson Ranch, CA (US); Kevin L. Morgan, Simi Valley, CA (US); John R. Helland, Saugus, CA (US); Sheldon Williams, Green Valley, CA (US); Kerwyn Schimke, Simi Valley, CA (US); Christopher R. Jenney, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 582 days.

(21) Appl. No.: 10/154,893

(22) Filed: May 22, 2002

(65) Prior Publication Data

US 2003/0220677 A1   Nov. 27, 2003

(51) Int. Cl.[7] .................................................. A61N 1/05
(52) U.S. Cl. ..................................................... 607/122
(58) Field of Search ............................... 600/372–374, 600/377, 381; 607/115, 116, 119, 122, 123, 607/125

(56) References Cited

U.S. PATENT DOCUMENTS

| | | | | |
|---|---|---|---|---|
| 4,498,482 A | * | 2/1985 | Williams | 607/122 |
| 4,643,202 A | | 2/1987 | Roche | 128/786 |
| 4,739,768 A | | 4/1988 | Engelson | 128/658 |
| 4,759,378 A | | 7/1988 | Swendson et al. | 128/786 |
| 5,219,361 A | | 6/1993 | Von Recum et al. | 623/11 |
| 5,480,421 A | | 1/1996 | Otten | 607/122 |
| 5,545,204 A | * | 8/1996 | Cammilli et al. | 607/123 |
| 5,803,928 A | | 9/1998 | Tockman et al. | 607/122 |
| 5,925,073 A | * | 7/1999 | Chastain et al. | 607/122 |
| 5,935,160 A | | 8/1999 | Auricchio et al. | 607/122 |
| 6,070,104 A | | 5/2000 | Hine et al. | 607/123 |
| 6,192,280 B1 | * | 2/2001 | Sommer et al. | 607/122 |
| 6,249,708 B1 | | 6/2001 | Nelson et al. | 607/122 |
| 6,263,249 B1 | | 7/2001 | Stewart et al. | 607/116 |
| 6,389,320 B1 | | 5/2002 | Pianca | 607/122 |
| 6,408,213 B1 | * | 6/2002 | Bartig et al. | 607/122 |
| 6,662,055 B1 | * | 12/2003 | Prutchi | 607/122 |
| 2003/0181966 A1 | * | 9/2003 | Morgan | 607/122 |

* cited by examiner

*Primary Examiner*—Kennedy Schaetzle
*Assistant Examiner*—Kristen Mullen

(57) ABSTRACT

An implantable stimulation lead is disclosed for placement in the coronary sinus region and its associated coronary vessels overlying the left side of a patient's heart. The lead comprises at least one proximal connector; at least one tissue stimulation electrode; at least one conductor coupled between the at least one proximal connector and the at least one stimulation electrode; and a lead body including a housing of insulating material enclosing the at least one conductor, the lead body having a relatively flexible distal portion of, for example, silicone rubber, having a length corresponding to the coronary sinus region of the heart, and a stiffer proximal portion of, for example, polyurethane. A robust transition joint comprising telescoped sections of the distal and proximal portions of the lead body couples the two portions of the lead body.

Also provided is a versatile lead delivery system including a stylet stop disposed within the distal portion of the lead body. The stylet stop defines an aperture dimensioned to pass a guide wire but not the enlarged distal tip of a stylet. The lead includes a tip electrode having a longitudinally extending bore dimensioned to permit passage of the guide wire through the tip electrode.

41 Claims, 11 Drawing Sheets

IMPLANTABLE CORONARY SINUS LEAD AND LEAD SYSTEM

FIELD OF THE INVENTION

The present invention relates generally to body implantable stimulation leads and lead systems. More particularly, the invention relates to body implantable stimulation leads designed to be placed intravenously in the coronary sinus region of the heart for left heart pacing, sensing and/or defibrillation, and to associated lead systems including devices for delivering such leads to target implantation sites.

BACKGROUND OF THE INVENTION

1. Left Side Stimulation and Sensing

The advantages of providing pacing therapies to both the right and left heart chambers are well established. For example, in four chamber pacing systems, four pacing leads, typically bipolar leads, are positioned for both pacing and sensing in the respective heart chambers. To provide left side stimulation and sensing, leads are transvenously implanted in the coronary sinus region, for example, in a vein such as the great vein or the left posterior ventricular (LPV) vein or other coronary veins proximate the left ventricle of the heart. Such placement avoids the risks associated with implanting a lead directly within the left ventricle which can increase the potential for the formation of blood clots which may become dislodged and then carried to the brain where even a small embolism could cause a stroke. As used herein, the phrase "coronary sinus region" refers to the coronary sinus, great cardiac vein, left marginal vein, left posterior ventricular vein, middle cardiac vein, and/or small cardiac vein or any other coronary vein accessible by way of the coronary sinus.

The tip electrode of a lead implanted in the coronary sinus region can pace and sense left side ventricular activity. When such a lead includes a second electrode proximal of the tip electrode and residing in a coronary vein overlying the left ventricle closely adjacent to the left atrium of the heart, pacing and sensing of left atrial activity is made possible. Moreover, the lead may include one or more electrodes for the delivery of electrical shocks for terminating tachycardia and/or fibrillation. Such cardioverting/defibrillating electrodes may be used by themselves or may be combined with pacing and/or sensing electrodes.

The implantation of a lead in the coronary sinus region is often difficult, however, because of the extreme curvatures in the coronary vessels, their narrowness, anomalies in the vascular anatomy because of disease, and the number of veins which may communicate with the desired lead feed path.

Current leads which are implanted in the coronary venous system for left heart pacing and/or defibrillation are typically designed with one type of primary insulation such as silicone rubber along the lead body. This provides for leads with uniform handling characteristics. Some leads use silicon rubber as the inner, primary insulation and an outer sheath of polyurethane for mechanical protection. Although this approach works reasonably well the result of using just one insulation is that the insulation, if it is silicon rubber, is flexible but can be prone to abrasion. On the other hand, where a typical, currently available biostable, biocompatible polyurethane is used to insulate the lead, and particularly the distal end portion thereof, the lead will be too stiff to permit ease of maneuvering of the distal end portion within the coronary vessels. Leads which use both materials, with silicon rubber as the inner insulation and polyurethane as the outer insulation, have larger diameters and therefore are more difficult if not impossible to maneuver in the coronary venous system which, as indicated, has narrow veins with pronounced curvatures.

U.S. Pat. No. 4,643,202 discloses a cardiac pacing lead including an insulating sheath having a relatively short distal section made of a soft, flexible silicone elastomer and a longer proximal section made of a relatively stiff polyurethane material. The two sections are joined in telescoping fashion and sealed together at the joint with a medical grade adhesive. The patent does not disclose implantation of the pacing lead in the coronary veins on the left side of the heart; indeed, the lead diameter that is disclosed (about 2 mm) is too large to permit easy implantation of the lead deep into the coronary venous system.

2. Lead Delivery Systems

The distal end portions of the various types of leads that have been described are maneuvered into position relative to the heart tissue to be stimulated by means of a stylet or a guide wire or a combination of both and the use of such lead delivery expedients are well known in the art. Thus, a stylet is passed through the hollow connector pin at the proximal extremity of the lead through the central cavity or lumen of the coil conductors or through one of the lumens of a multilumen lead body to enable the implanting physician to orient the distal end portion of the lead and position the tip electrode via use of fluoroscopy to a desired location within the heart. The distal extremity of the stylet engages a plug or other fixed surface within the distal end portion of the lead assembly. To reduce frictional resistance to advancement of the stylet within the lead body, the lumen may include a thin wall PTFE tube through which the stylet is passed. (See, for example, U.S. Pat. No. 6,249,708.) Further, the stylet may comprise a steerable assembly so that a desired curvature in the distal end portion of the lead may be imparted during the introduction of the lead to guide it through curvatures in the patient's vascular system.

Stylets having enlarged tips designed to be received within a socket located in the distal end portion of a lead are also known. The socket releasably engages the enlarged distal end of the stylet and is the to increase control of lead positioning. See, for example, U.S. Pat. No. 5,480,421.

Another approach to the implantation of an intravenous lead is the use of a flexible guide wire along which the lead is slid to its destination. The guide wire, entrained within a lumen of the lead body, is advanced along a transvenous lead feed path to the desired position within the target vein. The lead is then pushed or advanced along the guide wire until the distal tip thereof reaches the desired position. The guide wire is then retracted and removed from the lead body. Advancement of the lead body along the guide wire may be accomplished by a stylet disposed in a lumen separate from and proximal of the lumen containing the guide wire. Such a combined stylet and "over the wire" pacing lead is disclosed in U.S. Pat. No. 5,803,928. The lead assembly and implantation technique disclosed in that patent are directed toward lead configurations adapted to be implanted in the coronary veins on the left side of the heart. In such a case, stylets often are not flexible enough to permit the lead to be implanted in the coronary vessels. A first lumen extends through the lead body from the proximal end toward the distal end but does not reach the distal tip. A flexible stylet inserted into that lumen engages a stop at the end of the lumen. Ahead of the stop in the distal or tip section of the lead is an orifice through the side of the lead body. A guide wire inserted through the side opening is advanced through a central opening in the distal tip of the lead. The guide wire is then used to steer the lead through the vasculature to the desired site for the electrode while the stylet, in engagement with the plug or fixed surface, is used to push the lead forward along the guide wire. Once the lead is in place the guide wire and the stylet are retracted and removed.

3. Lead Body Size

Many of today's intravascular endocardial leads are multipolar in which—besides an electrode at the tip—one or more ring electrodes are incorporated in the distal end portion of the lead for transmitting electrical stimulation pulses from the pulse generator to the heart and/or to transmit naturally occurring sensed electrical signals from the heart to the pulse generator. Thus, by way of example, in a typical bipolar lead having a tip electrode and a ring electrode, two concentric conductor coils with insulation in between are carried within the insulative sheath. One of the conductor coils connects the pulse generator with the tip electrode while the other conductor coil, somewhat shorter than the first conductor coil, connects the pulse generator with the ring electrode positioned proximally of the tip electrode. To reduce the outside diameter of multipolar leads, the individual conductor wires are each insulated and instead of being coaxial or concentric, all of the conductor wires are wound on the same diameter into a coil. Thus, in a multipolar lead employing this technique, the various wires are interleaved in a single coil, along the same coil diameter, thereby helping to reduce the overall diameter of the lead.

To further reduce the outside diameter of the lead body, lead bodies having multiple lumens have been developed. In place of coils wound from wire, multistrand, braided cable conductors may be used to connect the pulse generator at the proximal end of the lead with the tip and ring electrodes at the distal end of the lead. In some existing lead assemblies, a combination of a coil conductor and one or more cable conductors are utilized. In this case, the coil conductor is typically passed through a non-coaxial lumen, that is a lumen that is offset from the longitudinal axis of the lead body. Multilumen lead bodies may also carry defibrillation electrodes and associated combinations of coil or cable conductors.

Despite the advances made in the art, there remains a need for improved body implantable, intravenous stimulation/sensing leads and related lead systems that are especially suited for left side implantation.

SUMMARY OF THE INVENTION

Among other things, the invention provides a lead for left heart pacing and/or defibrillation which utilizes a soft, flexible material such as silicone rubber for the distal portion of the lead body and a stiffer material such as polyurethane for the proximal portion of the lead body. The use of such a composite design allows for a lead that is small in diameter throughout its length yet has a more desirable, more drivable stiffer proximal portion which is not prone to abrasion while at the same time providing a distal portion that is highly flexible for facilitating its placement in the coronary vessels overlying the left side of the heart.

In accordance with one specific, exemplary embodiment of the invention, there is provided an implantable stimulation lead suitable for placement in the coronary sinus region and its associated coronary vessels comprising at least one proximal connector, at least one tissue stimulation electrode such as a tip electrode and/or cardioversion/defibrillation electrode, and at least one conductor coupled between the at least one proximal connector and the at least one stimulation electrode. The lead further comprises a preferably multilumen lead body of insulating material enclosing the at least one conductor, the lead body having a relatively soft, flexible distal portion having a length corresponding to the coronary sinus region of the heart. The lead body further has a stiffer proximal portion extending from the at least one proximal connector to a proximal portion/distal portion interface at the proximal extremity of the distal portion of the lead body. The soft, distal portion of the lead body preferably comprises silicone rubber while the proximal portion of the lead body preferably comprises polyurethane.

In accordance with another aspect of the invention, the preferred lengths of the distal and proximal portions of the lead body are such that when the lead body is implanted, the proximal portion/distal portion interface resides just distal of the coronary os so that a distal end of the stiffer proximal portion resides in the coronary sinus. Still further, the lead body may be isodiametric or the flexible distal portion of the lead body may have an outer diameter that is smaller than that of the stiffer proximal portion so as to facilitate access to narrow, distal coronary vessels.

Pursuant to yet another specific embodiment of the invention, the distal portion of the lead body may be configured to engage the wall of the coronary vessel in which the distal portion of the lead body is implanted to passively anchor the distal portion of the lead body in the coronary vessel. For example, the distal portion of the lead body may be configured with at least one S-shaped bend. Further, at least a portion of the outer surface of the distal portion of the lead body may be texturized to aid in passively anchoring the distal portion.

In accordance with another aspect of the invention, the relatively flexible distal portion of the lead body is coupled to the stiffer proximal portion by means of a robust joint that resists separation of the proximal and distal portions of the lead body. Pursuant to a preferred form of this aspect of the invention, the joint comprises telescoped sections of the distal and proximal portions of the lead body. More specifically, the telescoped sections of the distal and proximal portions of the lead body comprise a cored out section of the distal portion of the lead body and a reduced diameter section of the proximal portion of the lead body. Further, the cored out section of the distal portion of the lead body may have an inner diameter that is smaller than the outer diameter of the reduced diameter section of the proximal portion of the lead body so that an interference fit exists between the cored out and reduced diameter sections. Given these relative diameters, there will be a tendency for the telescoped sections to increasingly grip together if an attempt is made to pull apart the distal and proximal portions of the lead body. This "sphinctering" action further assures that the lead body portions will not separate when tension is applied to the proximal portion of the lead body during lead explantation.

Still further, the above-mentioned at least one conductor may comprise the series combination of a cable conductor residing in the proximal portion of the lead body and a more flexible coil conductor disposed within the distal portion of the lead body. The use of a flexible coil conductor in the distal portion of the lead body further facilitates left side placement of that portion.

The coil conductor contained within the distal portion of the lead body will in most instances comprise MP35N, the most commonly used alloy for such a conductor. A disadvantage of MP35N is that when it comes in contact with polyurethane (the preferred material for the proximal portion of the lead body), metal ions such as cobalt ions from the MP35N tend to migrate into the polyurethane attacking and degrading that material. The present invention addresses this problem by providing the cored out section of the distal portion of the lead body with a length greater than that of the reduced diameter section of the proximal portion of the lead body. The space so defined between the distal ends of the reduced diameter and cored out sections is filled with medical adhesive thereby isolating the proximal end of the MP35N coil conductor from the polyurethane proximal portion of the lead body.

Still further, the joint coupling the lead body portions may include a transition tube, the coil conductor having a proximal end including a plurality of windings disposed about the transition tube and the cable conductor having a distal end in electrical communication with the plurality of windings. Further in accordance with this aspect of the invention, the transition tube has a distal part and a proximal part, the windings at the proximal end of the coil conductor being disposed about the distal part of the transition tube. A tubular liner of low friction material such as PTFE through which a lead body-steering stylet or guide wire may be passed, and disposed within a lumen in the proximal portion of the lead body, has a distal end slipped over the proximal part of the transition tube.

In accordance with still another feature of the invention, a versatile lead delivery system is provided including a stylet stop disposed within the distal portion of the lead body. The stylet stop defines an aperture dimensioned to pass a guide wire but not the enlarged distal tip of a stylet. The lead includes a tip electrode having a longitudinally extending bore dimensioned to permit passage of the guide wire through the tip electrode. Accordingly, either a stylet or a guide wire can be used to deliver the distal portion of the lead body to its destination in the coronary vasculature.

Preferably, the stylet stop comprises a tubular member having an inner wall, the tubular member including an annular protuberance projecting inwardly from the inner wall of the tubular member, the annular protuberance defining the aforementioned aperture, whereby the stylet, inserted in a lumen of the lead, is advanced within the lumen until the enlarged distal tip of the stylet engages the annular protuberance.

BRIEF DESCRIPTION OF THE DRAWINGS

The foregoing and other objects, features and advantages of the invention will be evident to those skilled in the art from the detailed description of the invention, below, taken together with the accompanying drawings, in which.

DETAILED DESCRIPTION OF THE INVENTION

The following description presents preferred embodiments of the invention representing the best mode contemplated for practicing the invention. This description is not to be taken in a limiting sense but is made merely for the purpose of describing the general principles of the invention whose scope is defined by the appended claims. Moreover, the context in which the invention is principally shown and described herein, that is, bipolar pacing and sensing leads, is illustrative only; it will be understood by those skilled in the art that the invention has applicability to a wide variety of body implantable lead types, including unipolar and multipolar leads for both pacing and sensing and optionally for providing cardioversion/defibrillation stimuli.

Figure 1:
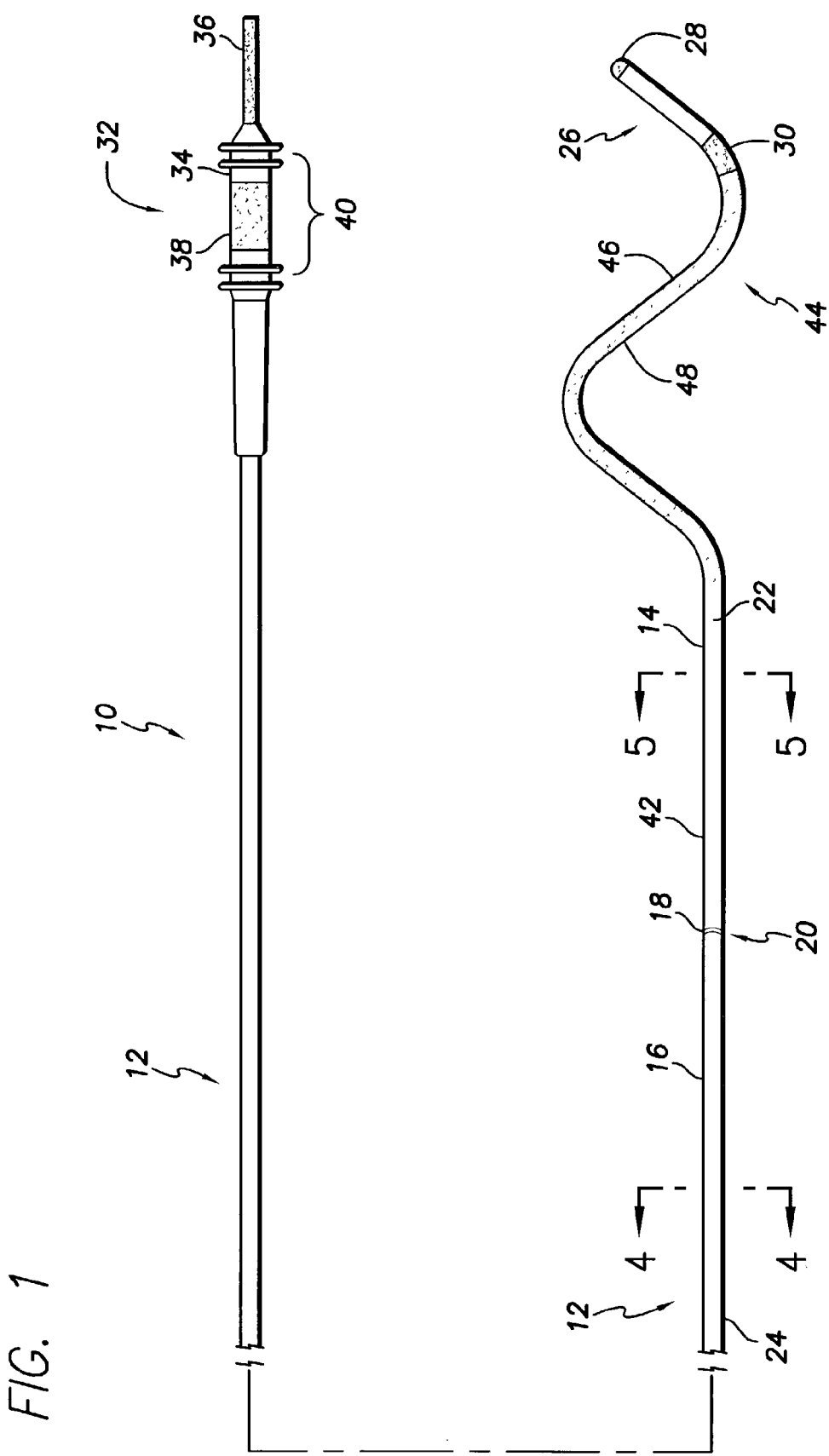
FIG. 1 is a bipolar endocardial pacing and sensing lead incorporating the present invention.

With reference to FIG. 1, there is shown a bipolar endocardial pacing and sensing lead 10 in accordance with a preferred embodiment of the present invention. The lead 10 includes a lead body 12 comprising a distal portion 14 and a proximal portion 16 joined or coupled at an interface 18 forming part of a coupling or transition joint 20. The distal portion 14 of the lead body is covered by a tubular sheath or housing 22 made of an insulating, biocompatible, biostable material that is relatively soft, flexible and pliable, preferably silicone rubber. The proximal portion 16 of the lead body is stiffer than the distal portion and this portion 16 of the lead body is covered by a tubular, insulating sheath or housing 24 made of a relatively stiff insulating, biocompatible, biostable material such as polyurethane. For left side placement, the softer, more flexible distal portion 14 of the lead body preferably has a length corresponding to the coronary sinus and its associated coronary vessels overlying the left side of the heart, ranging from approximately 4 cm to approximately 20 cm, and preferably from about 6 cm to about 10 cm. The stiffer proximal portion 16 will then preferably have a length so that when the lead is implanted, that portion will extend to a location just distal of the coronary os, that is, the distal extremity of the proximal portion at the interface 18 will reside in the coronary sinus.

The distal portion of the lead body includes a distal tip 26 incorporating a tissue stimulating tip electrode 28. Disposed proximally of the tip electrode along the distal portion of the lead body is a ring electrode 30 serving to sense electrical impulses produced by the heart tissue. It is desirable to have the distance between the tip and sensing electrodes sufficiently small to allow both of these electrodes to be placed in a target coronary vessel such as the LPV vein. Such placement of the electrodes 28 and 30 ensures achieving electrical capture of the left ventricle. Electrical capture is defined as the successful depolarization and contraction of a cardiac chamber (for example, atrium or ventricle) in response to an electrical stimulation pulse generated by an implantable device such as a pacemaker or an implantable cardioverter/defibrillator (ICD). Other electrode configurations can, of course, be employed. For example, an alternate arrangement may include the use of two ring electrodes for sensing electrical signals generated by the heart. Still another electrode configuration may include use of the tip electrode for performing unipolar sensing, pacing and/or cardioversion/defibrillation. The kind of electrode configuration used will depend on the particular application and accordingly any electrode configuration known in the art (for example, pacing/sensing electrodes or defibrillation electrodes or any combination thereof at the lead tip or adjacent to the tip) may be utilized. With the electrode configuration shown in FIG. 1, an implantable cardiac device, such as a pacemaker or ICD, not shown in FIG. 1, is connected to the tip electrode 28 and the ring electrode 30 to perform bipolar sensing, pacing and/or cardioversion/defibrillation of the left ventricle through the coronary sinus region of the heart.

The lead 10 has a proximal end 32 incorporating a connector assembly 34 for coupling the lead body 12 to a pacemaker or an ICD. The connector assembly 34 includes a hollow or tubular connector pin 36 electrically coupled to the tip electrode 28 and a ring contact 38 electrically coupled to the ring electrode 30. The connector assembly 34 of the lead is received within a receptacle of the pacemaker or ICD and to prevent ingress of body fluids into the receptacle, the connector assembly may be provided with spaced sets of seals 40 in accordance with well-known arrangements in the art. Further, in accordance with well-known implantation techniques, a stylet or guide wire for delivering and steering the distal portion 14 of the lead body during implantation is inserted into the lead body through the hollow connector pin 36.

In accordance with one form of the lead of the invention, the lead body may be isodiametric, that is, the outside diameters of the proximal and distal portions 14 and 16 of the lead body 12 may be the same throughout the entire length of the lead body. Alternatively, as illustrated in FIG. 1, the outside diameter of the distal portion 14 of the lead body may be less than that of the proximal portion 16 with a taper 42 being provided for this purpose distally of the interface 18 between the distal and proximal portions.

By way of example and not limitation, the outside diameter of the distal portion 14 of the lead body may range from about 0.026 inch (2F) to about 0.091 inch (7F). The outside diameter of the proximal portion 16 of the lead body can range from about 0.026 inch (2F) to about 0.130 inch (10F). The preferred outside diameters of the distal and proximal portions are about 0.050 inch and about 0.080 inch, respectively. Further, the softer and more flexible distal portion 14 may have a length ranging from about 4 cm to about 20 cm, preferably from about 6 cm to about 10 cm.

The cross-sectional configuration of the lead body 12 may accommodate various combinations of coil and/or cable conductor combinations, including, for example, a unipolar coil, bipolar coaxial coils, a unipolar cable, bipolar cables, or multilumen combinations of coils and/or cables. As will be further explained below, in accordance with the preferred embodiment of the present invention, the lead body comprises multilumen housings enclosing a combination of cables in the proximal portion 16 of the lead body and one or more coil conductors in the distal portion 14 of the lead body. The use of coil conductors within the distal portion of the lead body provides that portion with greater flexibility further facilitating its maneuvering around sharp bends and corners in the coronary venous vasculature.

In accordance with well known techniques, the lead body 12 may have a lubricious coating on most or all the lead body to facilitate its movement through a left heart delivery introducer.

As indicated, the lead body housings 22 and 24 are fabricated of materials lending stiffness to the proximal portion 16 while the distal portion 14 is relatively softer and more flexible. For example, the silicone rubber from which the distal portion housing 22 is fabricated may have a Shore hardness number ranging from 35A to 90A. In contrast, the Shore hardness number of the stiffer polyurethane housing 24 of the proximal portion of the lead body may range, for example, from 45A to 60D.

As already indicated, the distal portion 14 of the lead body may carry only pacing and sensing electrodes, only cardioverting/defibrillating electrodes or a combination of pacing, sensing and cardioverting/defibrillating electrodes. Where defibrillating electrodes are included these may be of conventional coil design or, for greater flexibility, they may comprise spaced apart, relatively short metallic rings or may be made of a conductive polymer or conductive coatings for greater flexibility. Further, in accordance with well known lead designs, the distal tip 26 of the lead body may be curved, comprising either a single curve or a compound curve, to facilitate advancing and steering the lead tip well into the coronary veins.

The distal portion 14 of the lead body 12 includes passive fixation means 44 to help anchor the distal portion 14 within a target vessel of the coronary sinus region. The passive fixation or anchoring means 44 may comprise one or more preformed humps, spirals, S-shaped bends or other configurations manufactured into the distal portion of the lead body. In the specific exemplary embodiment of the invention shown in FIG. 1, the distal portion of the lead body has a single S-shaped bend 46 so that when the distal portion 14 of the lead body is in place within a coronary vessel, there will be biased contact between the S-shaped bend 46 and the inner wall of the target vessel so as to create frictional forces sufficient to wedge or anchor the lead and preventing its displacement or dislodgement. Alternatively, the passive fixation means may comprise—either by itself or in combination with humps, spirals, bends, or the like—one or more soft, flexible protuberances that also tend to wedge the distal portion of the lead body in the target coronary vein. In either case, such passive fixation means 44 biases the distal portion 14 against the vessel wall. The passive fixation means can further include texturization 48 of the distal portion of the lead body to promote rapid blood clotting and resulting fibrotic tissue growth about the distal portion to help anchor that portion in place. Such texturization may be formed by grit blasting or abrading the outer surface of the lead body. Still further, the passive fixation means may be located along either the distal tip region of the distal portion of the lead body or the region of the distal portion situated in the coronary sinus in which case the fixation means would have a larger dimension consistent with the larger size of the coronary sinus. The fixation means can also comprise an active fixation mechanism such as a helix. It will be evident to those skilled in the art that any combination of the foregoing fixation or anchoring means can be employed.

In summary then, the invention provides for a lead for left heart pacing and/or defibrillation which utilizes a suitable type of silicone rubber (for example, Dow Corning Q7-4780) for the housing of the distal portion of the lead body and a suitable type of polyurethane (for example, Dow Chemical Pellethane 2363-55D) for the housing of the proximal portion. The use of such a composite design allows for a lead that is small in diameter throughout its length yet has a stiffer proximal portion which is not prone to abrasion while at the same time providing a distal portion that is highly flexible.

Figure 5:
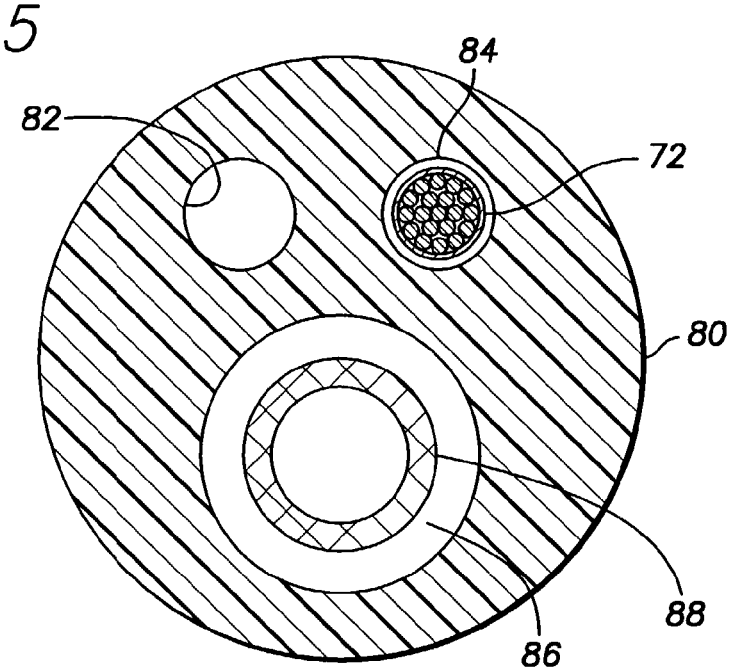
FIG. 5 is a transverse cross section view of the distal portion of the lead of FIG. 1 as seen along the lines 5—5 in FIGS. 1–3.

Although, as noted, the lead body may have various cross-sectional configurations, in accordance with a preferred embodiment of the invention, both the distal and proximal portions 14 and 16 of the lead body 12 comprise tubular, multilumen housings. With reference now to FIGS. 2–5, the proximal portion 16 of the lead body comprises a trilumen housing 60 defining three axially or longitudinally extending, parallel passages or lumens 62, 64 and 66 one of which (66) is larger than the other two and encloses a low friction liner 68 of PTFE, for example, through which a stylet or guide wire may be passed for delivering and steering the distal portion 14 of the lead body during implantation thereof. The remaining two lumens 62 and 64 which, as indicated, are smaller than the lumen 66 enclosing the liner, carry braided cables 70 and 72, respectively, typically of MP25N or MP35N/Ag alloy, coated or uncoated with a lubricious film. The cable conductor 70 forms a portion of the electrical connection between the tip electrode 28 and the connector pin 36 at the proximal end of the lead. The other cable conductor 72 provides part of the electrical connection between the sensing ring electrode 30 along the distal portion of the lead body and the ring contact 38 on the connector assembly. The distal portion 14 of the lead body, like the proximal portion 16, comprises a trilumen housing 80 defining three axially or longitudinally extending, parallel passages or lumens 82, 84 and 86 one of which (86) is larger than the other two and carries a preferably multifilar coil conductor 88 forming the other part of the electrical connection between the connector pin 36 and the tip electrode 28. The lumens of the proximal and distal trilumen housings are in longitudinal alignment. The hollow interior or lumen 90 of the coil conductor 88 is in longitudinal alignment with the liner 68 to provide access for a stylet or guide wire used during lead implantation. The coil conductor 88 transmits electrical signals between the pacemaker or ICD and the tip electrode 28 and, as noted, these electrical signals may comprise pacing stimuli to the heart tissue engaged by the tip electrode as well as sensed electrical signals emanating from the heart. As best seen in FIG. 5, the small lumen 84 within the distal housing 80 includes a cable conductor connecting the ring electrode and the ring contact.

Figure 2:
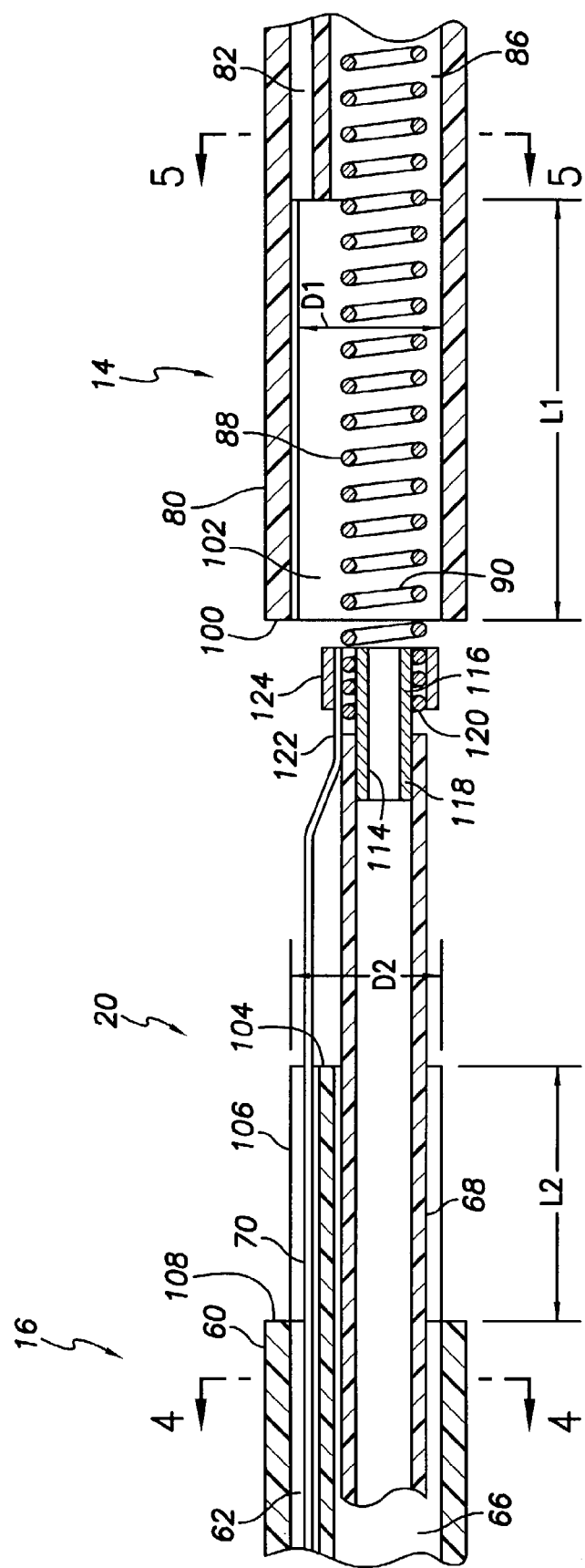
FIG. 2 is an exploded, side view of a portion of the lead of FIG. 1 showing details of a transition joint forming a part thereof.
Figure 3:
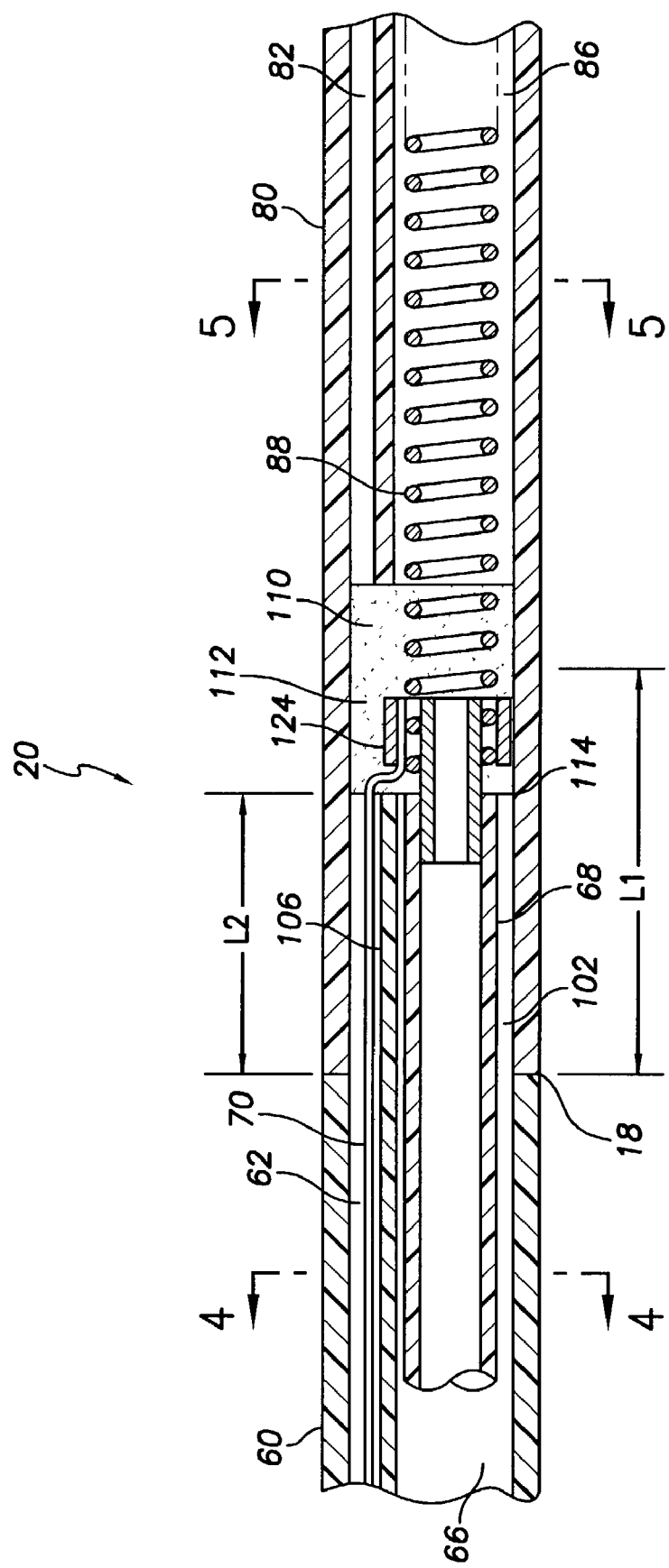
FIG. 3 is a side view, in cross section of the transition joint of FIG. 2 shown in its assembled configuration.
Figure 4:
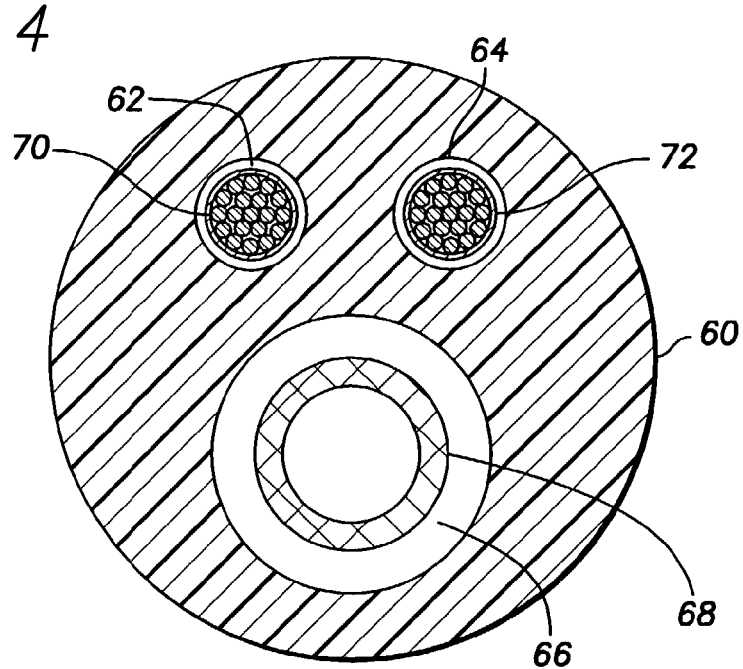
FIG. 4 is a transverse cross section of the lead of FIG. 1 as seen along the lines 4—4 in FIGS. 1–3.

FIGS. 2 and 3 show details of a preferred transition joint 20, essentially in the form of a lap joint, especially suitable for the composite lead of the invention. The transition joint 20 provides a robust coupling for joining the soft, flexible, preferably silicone rubber distal portion 14 of the lead body with the stiffer, preferably polyurethane proximal portion 16 of the lead body. Among other things, the joint 20 provides for transitions from the PTFE liner 68 and the cable conductor 70 to the coil conductor 88.

More specifically, the distal portion 14 of the lead body has a proximal extremity defining a transverse, annular interface surface 100. The distal portion is cored out along a section 102 extending distally from the proximal extremity 100 of the distal portion. The cored out section 102 has a length L1 and an internal diameter D1. The proximal portion of the lead body includes a distal extremity 104 and a reduced diameter section 106 extending proximally from the distal extremity of the proximal portion to a proximal portion interface surface in the form of a shoulder 108. The reduced diameter section 106 on the proximal portion of the lead body has a length L2, shorter than the length L1, and an outside diameter D2 that is greater than the diameter D1. When the cored out and reduced diameter sections 102 and 106 are joined in telescoped relationship, as shown in FIG. 3, the interface surfaces 100 and 108 are in abutment. The relative lengths L1 and L2 of the telescoped sections 102 and 106 are such that in the assembled configuration shown in FIG. 3, a space 110 is defined between the distal extremity of the proximal portion and the distal extremity of the cored out section. The space 110 is filled with medical adhesive 112 for the reason which will be now explained.

The coil conductor 88 contained within the large lumen 86 of the distal portion of the lead body will in most instances comprise MP35N or MP35N/Ag (hereinafter referred to only as "MP35N"), the most commonly used alloy for such a conductor. Other conductive materials may, of course, be used for the coil conductor but MP35N presently remains the material of choice. A disadvantage of MP35N is that when it comes in contact with polyurethane (the preferred material for the proximal portion housing 60), metal ions (especially cobalt ions) from the MP35N tend to migrate into the polyurethane attacking and degrading that material. A known way for isolating MP35N conductors from polyurethane is to coat the conductor with platinum. That remedy, however, increases the coil diameter and can be costly. In the present invention, the coil conductor 88 contained within the silicone rubber distal portion of the lead body is isolated from the polyurethane constituting the housing 60 of the proximal portion by filling the space 110 within the joint 20 with the medical adhesive 112. Such adhesive is sufficiently flexible so that it does not significantly decrease the flexibility of the transition joint.

Medical adhesive may be used to bond the overlapping telescoped sections 102 and 106 of the distal and proximal portions so that separation of these portions will be resisted when tension is applied along the transition joint 20. The overlapping surfaces may be chemically etched and/or primed to enhance the bond. Further, given the relative sizes of the diameters D1 and D2, with D2 being larger than D1, there will be a tendency for the telescoped sections 102 and 106 to increasingly grip together if an attempt is made to pull the distal and proximal portions of the lead body apart. This "sphinctering" action further assures that the lead body portions 14 and 16 do not separate when tension is applied to the proximal portion of the lead body during explantation thereof.

By way of example and not limitation, the overlapping sections of the transition joint may have the following dimensions:

L1=0.35 inch
L2=0.2 inch
D1=0.060 inch
D2=0.062 inch

The area of the bonded, overlapping surfaces is preferably at least 0.006 sq. inch (4 sq. mm) although other surface areas are usable depending upon the specific diameter and length of the overlapping sections as well as the specific materials employed.

The transition joint 20 includes a transition tube 114 having a distal end 116 and a proximal end 118. The distal end 116 of the transition tube is inserted within several windings 120 of the coil conductor 88 at the proximal end thereof while the distal end of the tubular liner 68 is slipped over the proximal end 118 of the transition tube. The tip electrode cable conductor 70 includes a distal end 122 in contact with the windings 120 wound about the transition tube 114 and securely clamped thereto by means of a crimp tube 124 surrounding the distal end of the transition tube. In this way, electrical continuity is established from the connector pin 36 to the tip electrode 28 via the cable conductor 70 and the coil conductor 88 which are electrically coupled within the joint 20. The electrical coupling between the distal end 122 of the braided cable conductor 70 and the windings 120 of the coil conductor 88 may be effected in other ways, for example, by means of a weld.

Figure 6:
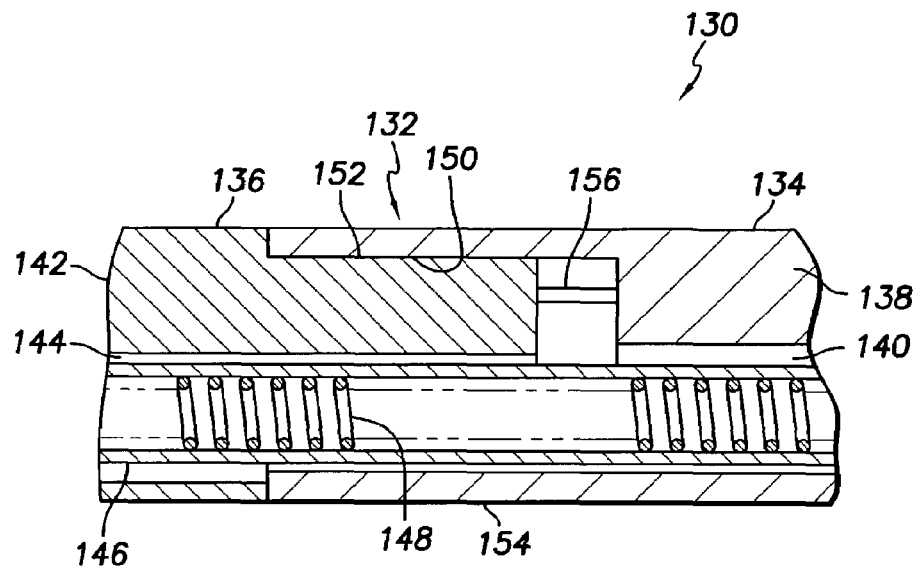
FIG. 6 is an axial cross section of a portion of a lead in accordance with an alternative embodiment of the invention illustrating another form that the transition joint coupling the distal and proximal portions of the lead body may take.

FIG. 6 shows a portion of a lead body 130 forming part of a lead in accordance with a first alternative embodiment of the invention. The lead body 130 includes a lap joint 132 coupling a distal portion 134 of the lead body with a proximal portion 136 thereof. The distal portion includes an insulative, tubular trilumen housing 138 of a soft, flexible material such as silicone rubber. The distal portion housing 138 defines a pair of small diameter longitudinally extending lumens (not shown) and a larger diameter longitudinal lumen 140. The proximal portion 136 of the lead body comprises an insulative, tubular trilumen housing 142 made of a stiffer material such as polyurethane. The proximal lead body housing defines a pair of small diameter lumens (not shown) and a larger diameter lumen 144, these lumens being in longitudinal alignment with those in the distal portion housing 138. Unlike the first embodiment, the embodiment of FIG. 6 includes a liner 146 of low friction material such as PTFE that extends through the large lumens 140 and 144 of both the proximal and distal portions along essentially the entire length of the lead body 130. The liner 146 houses a flexible coil conductor 148 coupling the hollow connector pin of a pacemaker/ICD connector assembly at the proximal end of the lead with a tip electrode. During implantation, a stylet or guide wire is passed through the lumen of the coil conductor 148 to permit maneuvering of the distal portion of the lead body into position relative to the tissue to be stimulated. The lap joint 132 of FIG. 6 is similar to that of the first embodiment in that the proximal end of the distal portion 134 of the lead includes a cored out section 150 dimensioned to receive, preferably in an interference fit, a reduced diameter section 152 extending distally from the distal end of the proximal portion 136 of the lead body. As before, the mating surfaces of the telescoped sections are preferably etched and/or primed and bonded with medical adhesive. The dimensions may be similar to those described in connection with the first embodiment.

In the alternative embodiment of FIG. 6, the proximal end of the distal portion 134 of the lead body includes a taper 154 along a part of the distal portion of the lead body so that the distal portion has a smaller outer diameter than the proximal portion, facilitating the maneuvering of the distal portion of the lead within the coronary venous vessels. A braided cable conductor 156 may be housed within one of the smaller lumens of the proximal and distal portions of the lead body for connecting a contact on the connector assembly at the proximal end of the lead body with, for example, a ring sensing electrode disposed along the distal portion of the lead body. The remaining small lumen of the trilumen portions may contain a second braided cable conductor for providing an electrical connection redundant with the first cable conductor. Alternatively, the second cable conductor may be used, for example, to connect a contact on the connector assembly of the lead with a defibrillation electrode positioned along the distal portion of the lead body. The alternative embodiment of FIG. 6 is somewhat simpler than the embodiment shown in FIGS. 2 and 3 in that it eliminates the need for a cable conductor/coil conductor transition joint structure such as that of the first embodiment. The disadvantage of the embodiment of FIG. 6 is that with the presence of the cable conductors in the distal portion of the lead body, that portion may tend to be somewhat stiffer than the distal portion of the first embodiment.

Figure 7:
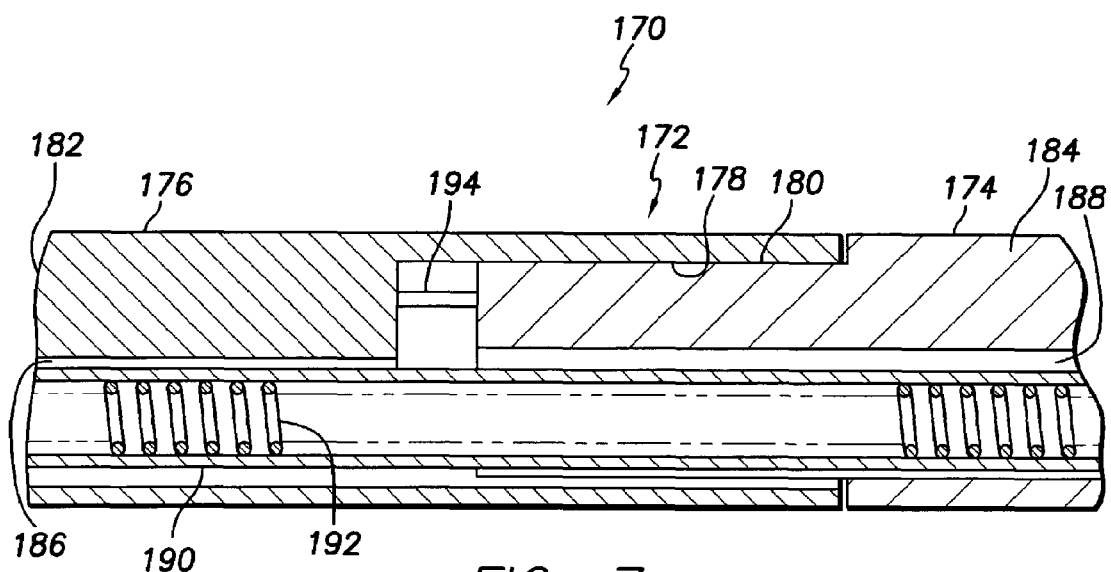
FIG. 7 is an axial cross section of a portion of a lead in accordance with a second alternative embodiment of the present invention showing yet another form that the transition joint joining the distal and proximal portions of the lead body may take.

FIG. 7 shows a portion of a lead body 170 comprising part of a lead in accordance with a second alternative embodiment of the invention. The lead body 170 includes a lap joint 172 for coupling a flexible distal portion 174 of the lead body with a stiffer proximal portion 176. The lap joint 172 of FIG. 7 is basically the reverse of that of FIG. 6 in that the distal end of the proximal portion 176 of the lead body is provided with a cored out section 178 and the proximal end of the distal portion 174 of the lead body is provided with a reduced diameter section 180 dimensioned to be telescopingly received, preferably with an interference fit, within the cored out section 178 of the proximal portion. As before, medical adhesive may be used to bond the overlapping, telescoped sections 178 and 180 whose surfaces are preferably etched to enhance the bond. Unlike the embodiment of FIG. 6, the lead body 170 of the embodiment of FIG. 7 is isodiametric although it will be obvious that as in the embodiment of FIG. 6, the distal portion of the lead body may have a smaller diameter than that of the proximal portion. As in the previous embodiments, the length of the overlap between the sections may be, for example, about 0.2 inch. Also, like the embodiment of FIG. 6, both the proximal and distal portions of the lead body comprise longitudinally aligned, multilumen, preferably trilumen, housings 182 and 184, respectively, with the larger lumens 186 and 188 containing a low friction liner 190 enclosing a tip electrode coil conductor 192 and the remaining two lumens containing at least one braided cable conductor 194 connected, for example, to a ring sensing electrode, all as previously described.

Figure 8:
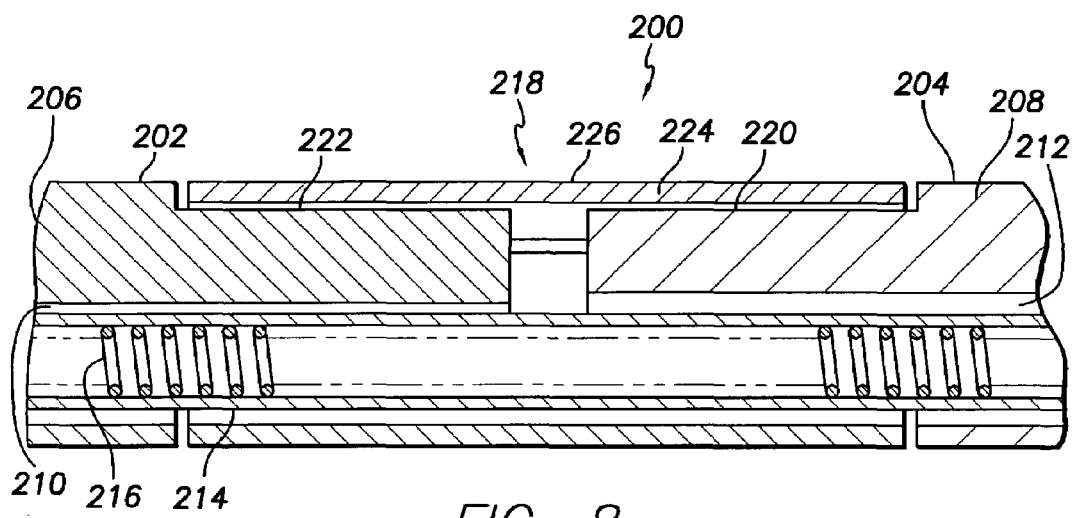
FIG. 8 is an axial cross section of a portion of a lead in accordance with a third alternative embodiment of the invention showing still another form that the transition joint coupling the distal and proximal portions of the lead body may take.

Turning now to FIG. 8, there is shown a portion of a lead body 200 in accordance with a third alternative embodiment of the invention. The lead body 200 includes a proximal portion 202 and a distal portion 204 comprising aligned trilumen housings 206 and 208, respectively, including, as before, large lumens 210 and 212 enclosing a low friction liner 214 extending the length of the lead body and enclosing a coil conductor 216 used, for example, to connect a tip electrode with a hollow pin electrode on the proximal end of the lead. The lead body 200 includes a lap joint 218 comprising a reduced diameter section 220 formed along the proximal end of the distal portion 204, a similar reduced diameter section 222 formed on the distal end of the proximal portion 202, and a sleeve 224 of, for example, silicone rubber, slipped over the reduced diameter sections 220 and 222 and bonded thereto by medical adhesive to join those sections. The sleeve 224 has an outer surface 226 flush with the outer surfaces of the proximal and distal portions 202 and 204 of the lead body to provide an isodiametric structure.

Figure 9:
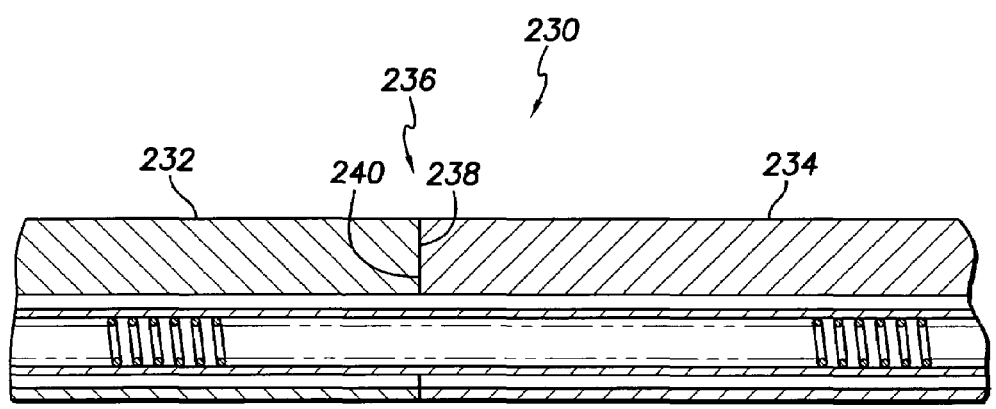
FIG. 9 is an axial cross section of a portion of a lead in accordance with a fourth alternative embodiment of the present invention showing a butt transition joint for coupling the distal and proximal portions of the lead body.

FIG. 9 shows a portion of a lead body 230 in accordance with a fourth alternative embodiment of the invention. The lead body 230 comprises a relatively stiff proximal portion 232 coupled to a softer, more flexible distal portion 234 by means of a butt joint 236 defined by a transverse surface 238 at the distal extremity of the proximal portion of the lead body bonded by medical adhesive to a transverse surface 240 formed on the proximal extremity of the distal portion of the lead. In all other respects, the lead body 230 may be the same as those of the previous embodiments.

Figure 10:
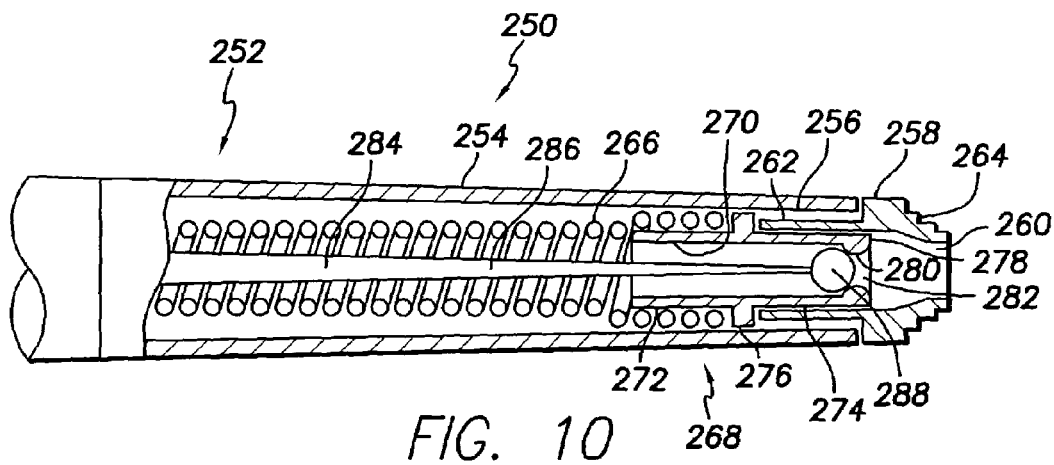
FIG. 10 is an axial cross section of the distal end of the lead of FIG. 1 showing the distal end of a stylet inserted therein.
Figure 11:
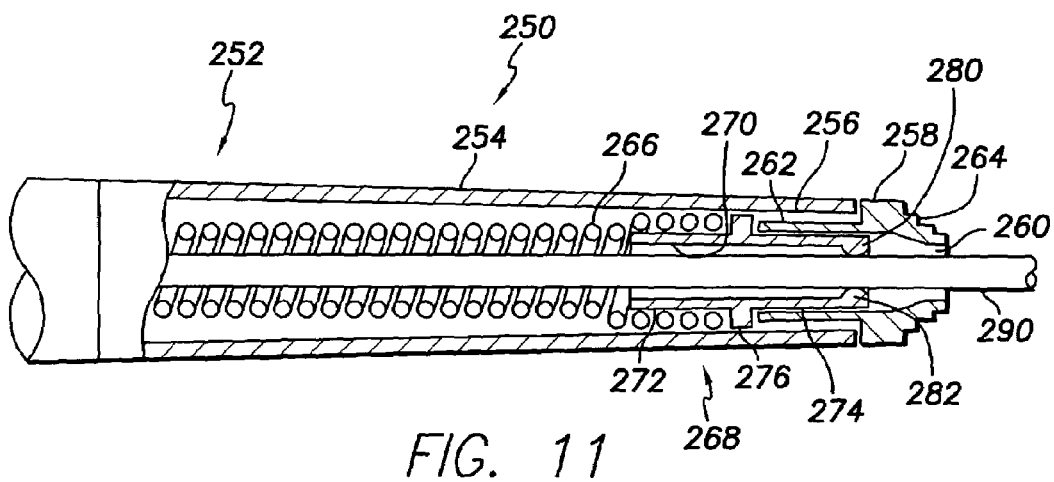
FIG. 11 is an axial cross section of the distal end of the lead of FIG. 1 including a lead-steering guide wire over which the lead has been slid.

With reference to FIGS. 10 and 11, there is shown a portion of a lead body 250 forming part of a bipolar endocardial pacing and sensing lead in accordance with another aspect of the present invention. The entire length of the lead body 250 may comprise a tubular, insulating sheath or housing made of an insulating, biocompatible, biostable material such as silicone rubber or polyurethane. However, pursuant to a preferred form of the lead, the lead body 250 comprises a relatively stiff proximal portion (not shown) of polyurethane, for example, coupled, as earlier described, to a softer, more flexible distal portion 252 to facilitate left side implantation. In that case, the distal portion 252 is preferably made of silicone rubber, and may include passive anchoring means in the form of one or more preformed humps, bends, spirals or other shape(s), as previously described.

The distal portion 252 of the lead body 252 includes a distal end 254 having a distal tip 256 incorporating an electrically conductive tip electrode 258. The tip electrode 258 comprises generally a tubular structure including a central, longitudinally extending bore 260 and a proximally extending tubular portion 262. The tip electrode 258 further includes an outer surface 264 for engaging the tissue to be stimulated. As shown in FIGS. 10 and 11, the outer surface 264 of the tip electrode may be stepped for increased surface area and to create edges which provide for enhanced electrical efficiency. As is known, the lead has a proximal end incorporating a connector assembly (not shown) including a hollow connector pin that is electrically coupled to the tip electrode 258 by means of a coil conductor 266 enclosed within the tubular insulative housing. A conductive, tubular weld element 268 electrically couples the coil conductor 266 to the tip electrode 258. The weld element 268 includes an inner cylindrical wall 270, a proximally extending section 272, a distally extending section 274 and an outwardly projecting flange 276 demarking these sections. The proximal section 272 is received within the lumen of the coil conductor 266; the coil conductor may be secured to the proximally extending weld element section 272 by laser welding, a crimp tube, or the like. The distally extending section 274 of the tubular weld element 268 terminates at a distal extremity 278 having an annular protuberance 280 projecting inwardly from the inner wall 270 of the weld element. The annular protuberance 280 defines a central aperture 282 coaxial of the longitudinal axis of the lead assembly. The annular protuberance 280 functions as a stylet stop.

The design of the distal end 254 of the lead body of FIGS. 10 and 11 provides for a particularly versatile left side delivery system. More specifically, the distal portion of the lead body may be maneuvered during implantation using either a stylet or a guide wire depending upon the destination of the lead, anatomical factors, and so forth. FIG. 10 shows a stylet 284 in place within the distal end 254. The stylet 284 has a tapered distal part 286 terminating at its distal extremity in an enlargement 288, for example, a ball. It will be seen that the ball 288 has a diameter greater than the aperture 282 defined by the annular protuberance 280 so that the ball of the stylet cannot pass therethrough. Advancement of the lead to the desired position is achieved by pushing the stylet 284, the ball thereof in turn pressing against the annular protuberance 280.

FIG. 11 shows the use of a guide wire 290 instead of a stylet for placement of the distal portion of the lead body 250. The diameter of the guide wire 290 is such that the guide wire is free to pass through the aperture 282 at the distal extremity of the tubular weld element 268 and to pass through the bore 260 of the tip electrode 258. In this fashion, the lead body may be moved along the guide wire 290 to its final destination in accordance with "over-the-wire" implantation techniques well known in the art. To effect a particular lead implantation, the stylet 284 and the guide wire 290 may, of course, be used alternately or in succession.

Figure 12:
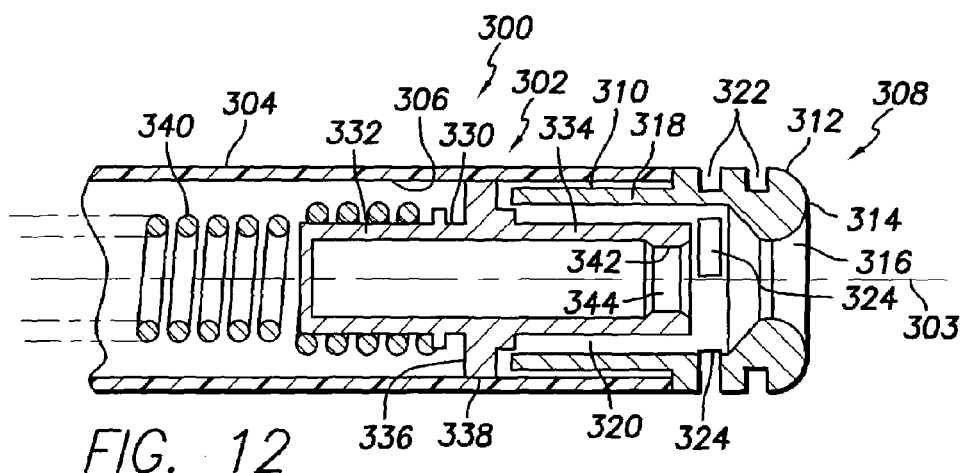
FIG. 12 is an axial cross section showing an alternative embodiment of the distal end of a lead in accordance with the invention.

With reference to FIG. 12, there is shown a simplified, axial cross section of a distal tip 300 alternative to that of FIGS. 10 and 11. The distal tip of FIG. 12 is carried at the distal end 302 of a distal portion of a lead body extending along a longitudinal axis 303. As before, the distal portion includes a tubular, soft, flexible, biostable, biocompatible, small diameter tubular housing 304 of, for example, silicone rubber facilitating left side implantation. The housing 304 includes at its distal extremity a cored out section 306 carrying a tip electrode 308. The tip electrode 308 includes a proximal end 310 and a distal end 312, the latter having a distal extremity defining an outer, active tissue stimulating electrode surface 314, annular in shape, thereby defining a central aperture 316. The stimulating electrode surface 314 is preferably rounded, as shown. The tip electrode includes a generally tubular section 318 having an interior chamber 320 extending between the proximal and distal ends of the tip electrode. The distal end of the tip electrode 308 may include one or more annular grooves 322 extending about the outer surface of the electrode. The chamber 320 communicates with at least one of the annular grooves 322 through one or more slots or bores 324, three such slots disposed equiangularly about the longitudinal axis 303 being shown in FIG. 12. The slots or bores 324 form an elution path for the passage of a drug stored in a drug impregnated plug (not shown) enclosed within the chamber 320 of the tubular section of the tip electrode. The drug may be one intended to counter thrombus formation, fibrosis, inflammation or arrhythmias, or any combination thereof, or to accomplish any desired localized purpose. For example, the drug dispensing plug may be loaded with a steroidal anti-inflammatory such as dexamethasone sodium phosphate serving to reduce the stimulation threshold by suppressing the tissues' typical inflammatory response to foreign material.

The electrode assembly of FIG. 12 further includes a weld element 330 having a distal portion 332 extending into the chamber 320 of the tip electrode and a proximal portion 334. The distally extending and proximally extending portions 332 and 334 of the weld element are separated by an annular flange 336 having an outer surface 338 in engagement with the inner surface of the cored out section 306 of the housing. The proximally extending tubular portion 334 of the weld element extends into the lumen of an electrical coil conductor 340 held in place by a crimp tube, welds, or a combination thereof. The coil conductor 340 extends through the lead body to a connector assembly on the proximal end thereof.

The weld element 330 includes a distal end having an annular protuberance 342 projecting inwardly from the inner wall of the weld element. The annular protuberance 342 defines a central aperture 344 coaxial of the longitudinal axis of the lead body and is in alignment with the aperture 316 in the distal end of the tip electrode 308. As in the previous embodiment of FIGS. 10 and 11, the annular protuberance 342 functions as a stylet stop and the aligned apertures allow passage of a guide wire in a manner already described. The distal portion of the lead body shown in FIG. 12 may carry only pacing and sensing electrodes, only cardioverting/defibrillating electrodes, or a combination thereof.

The distal tip structures of FIGS. 10 through 12 are universal in nature, that is, these structures allow use of either a stylet to drive the distal portion of the lead body into place or a guide wire to steer or direct the distal tip to its destination in an "over-the-wire" approach. As explained, these lead delivery techniques may also be used in combination, for example, with the stylet first and then the guide wire being used in succession, and then even switching back to the stylet to achieve an optimal tip position.

Figure 13:
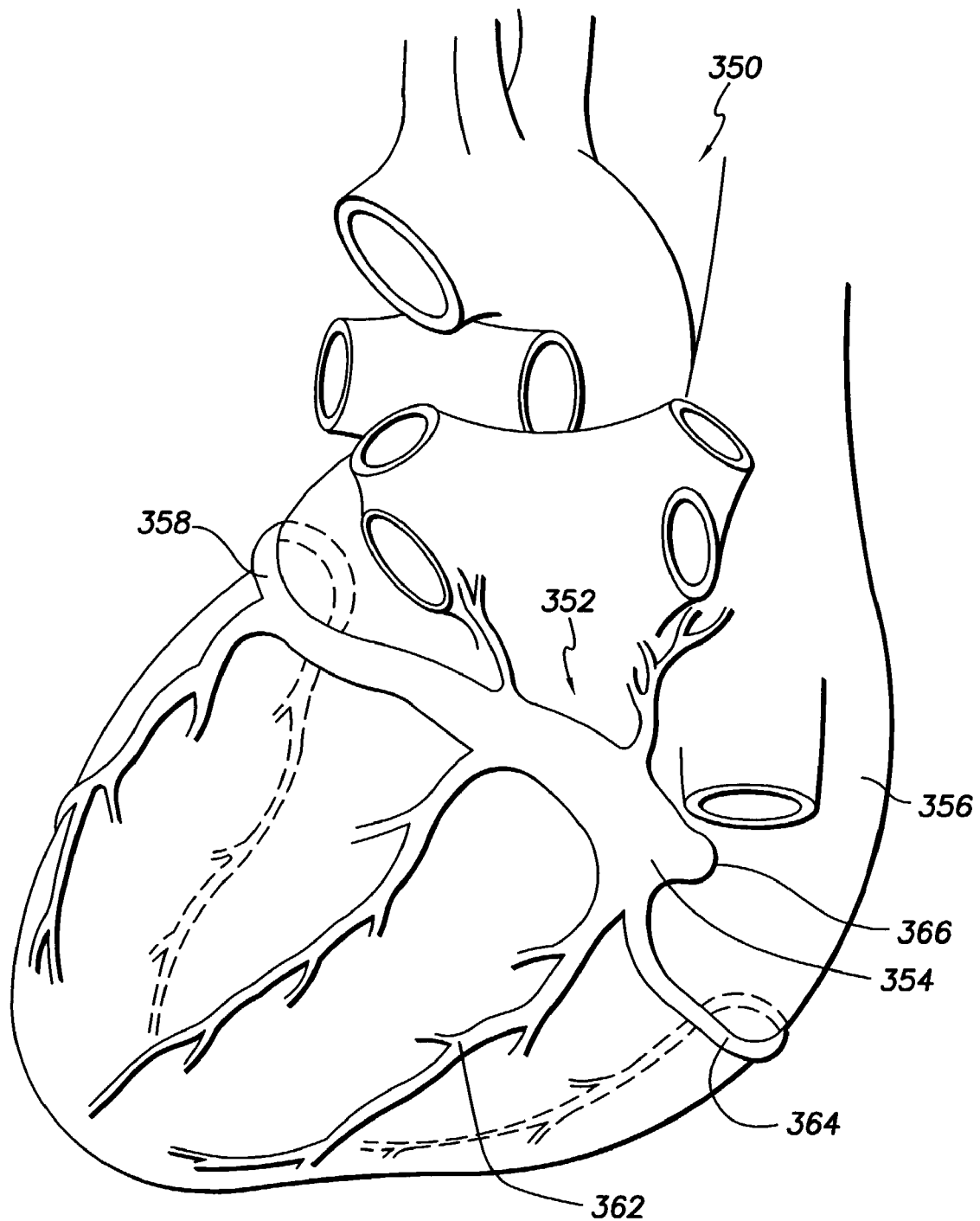
FIG. 13 is a perspective view of the left posterior region of the human heart.

FIG. 13 is a perspective view of the left posterior region of a heart 350 showing the relevant anatomy of the coronary sinus region 352. As shown in FIG. 13, the coronary sinus 354 is the main collecting vein of the heart which drains into the right atrium 356. Typically, the coronary sinus 354 runs from right to left in the posterior part of the coronary groove. The coronary sinus 354 connects to the great cardiac vein 358 and to the left posterior ventricular (LPV) vein (not shown in FIG. 13). The coronary sinus also connects to the middle cardiac vein 362 and small cardiac vein 364. The coronary sinus drains into the right atrium through an ostium or coronary os 366.

In one approach to the delivery of the lead to the coronary sinus and/or coronary veins, a "left heart lead delivery" work station or long percutaneous lead introducer adapted to reach into the coronary sinus is used to deliver the lead into the coronary sinus. The distal portion of the introducer may be curved, with various single or compound curves, to allow for ease in advancing the introducer through the coronary os and into the coronary sinus. The inserted introducer provides a conduit facilitating and supporting the placement of the lead in the coronary sinus and ultimately into the more distal cardiac veins within the coronary sinus region.

Figure 14:
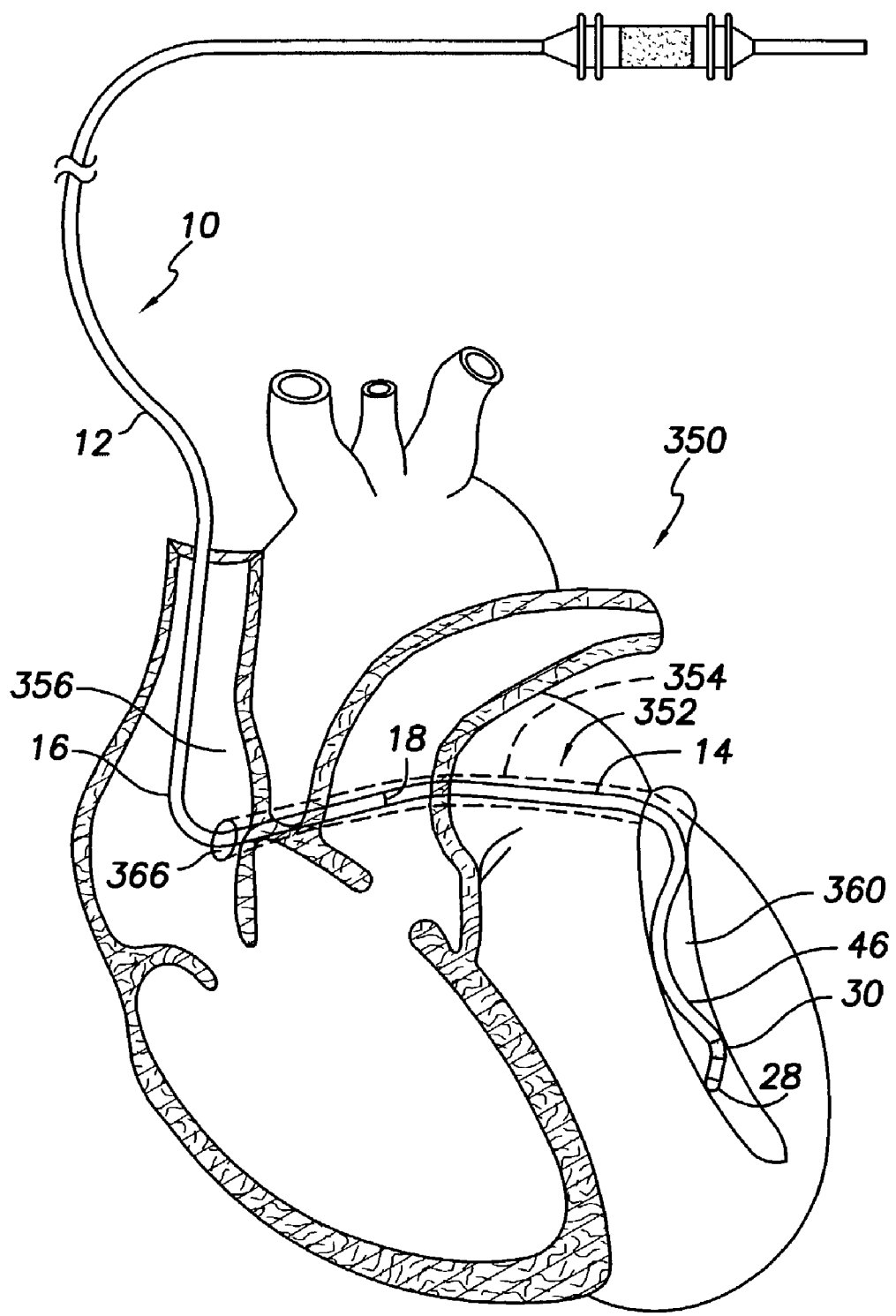
FIG. 14 is a perspective view of the anterior portion of the heart showing the distal portion of a lead body in accordance with the present invention implanted in the coronary sinus region thereof.

FIG. 14 is a simplified view of the anterior portion of the heart 350 showing a lead body in accordance with any of the above-described embodiments implanted in the coronary sinus region. The reference numerals in FIG. 14 are those of FIG. 1, used by way of example. It will be seen that the interface 18 of the flexible distal portion 14 and the stiffer proximal portion 16 of the lead body 12 lies distal of the coronary os 366; accordingly, the distal end of the proximal portion 16 of the lead body 12 resides in the coronary sinus 354, with the distal portion 14 of the lead body lying within the coronary sinus 354 and, in this particular example, with the tip and ring electrodes 28 and 30 placed within the LPV vein 360 in contact with the wall thereof. It will further be seen that the S-shaped bend 46 formed in the distal portion of the lead body has assumed its sinuous configuration so as to be biased against the wall of the LPV vein 360 thereby preventing displacement or dislodgment of the distal portion.

Figure 15:
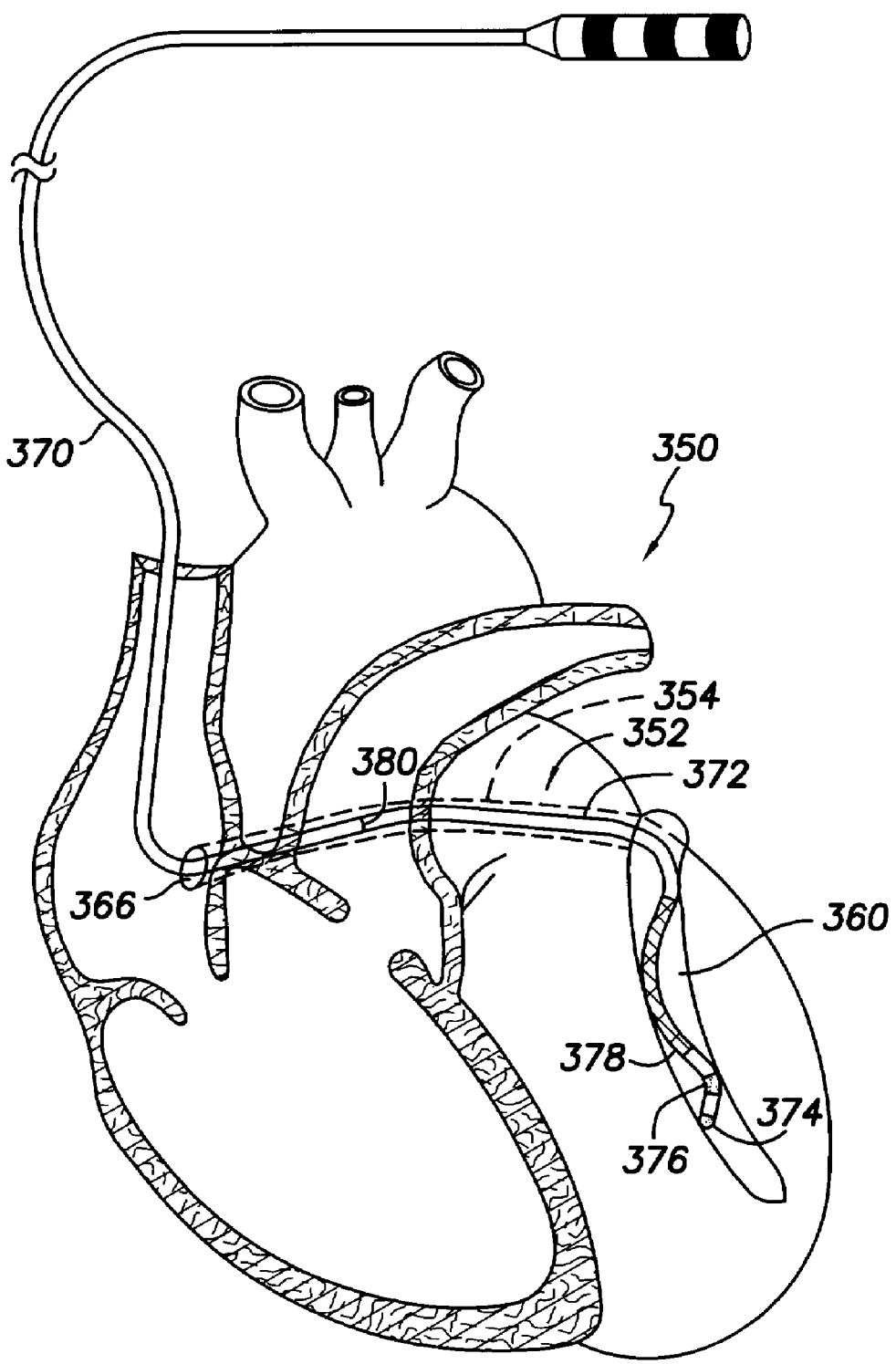
FIG. 15 is a perspective view of the anterior portion of the heart showing the distal portion of another lead body in accordance with the present invention implanted in the coronary sinus region thereof.

FIG. 15 is also a simplified view of the anterior portion of the heart 350 showing implanted in the coronary sinus region 352 thereof a lead body 370 that is a variation of the lead body of the embodiment of FIG. 1. The lead body 370 has a flexible distal portion 372 carrying, besides a tip electrode 374 and a ring sensing electrode 376, a cardioversion/defibrillator electrode 378. Although the lead body 370 can be implanted in any accessible vessel within the coronary sinus region 352, the lead body is shown placed, by way of example, within the LPV vein 360, with the electrodes 374, 376 and 378 in contact with the wall of the vein. As in the case of the embodiment of FIG. 14, the proximal portion/distal portion interface 380 is disposed distal of the coronary os 366.

Figure 16:
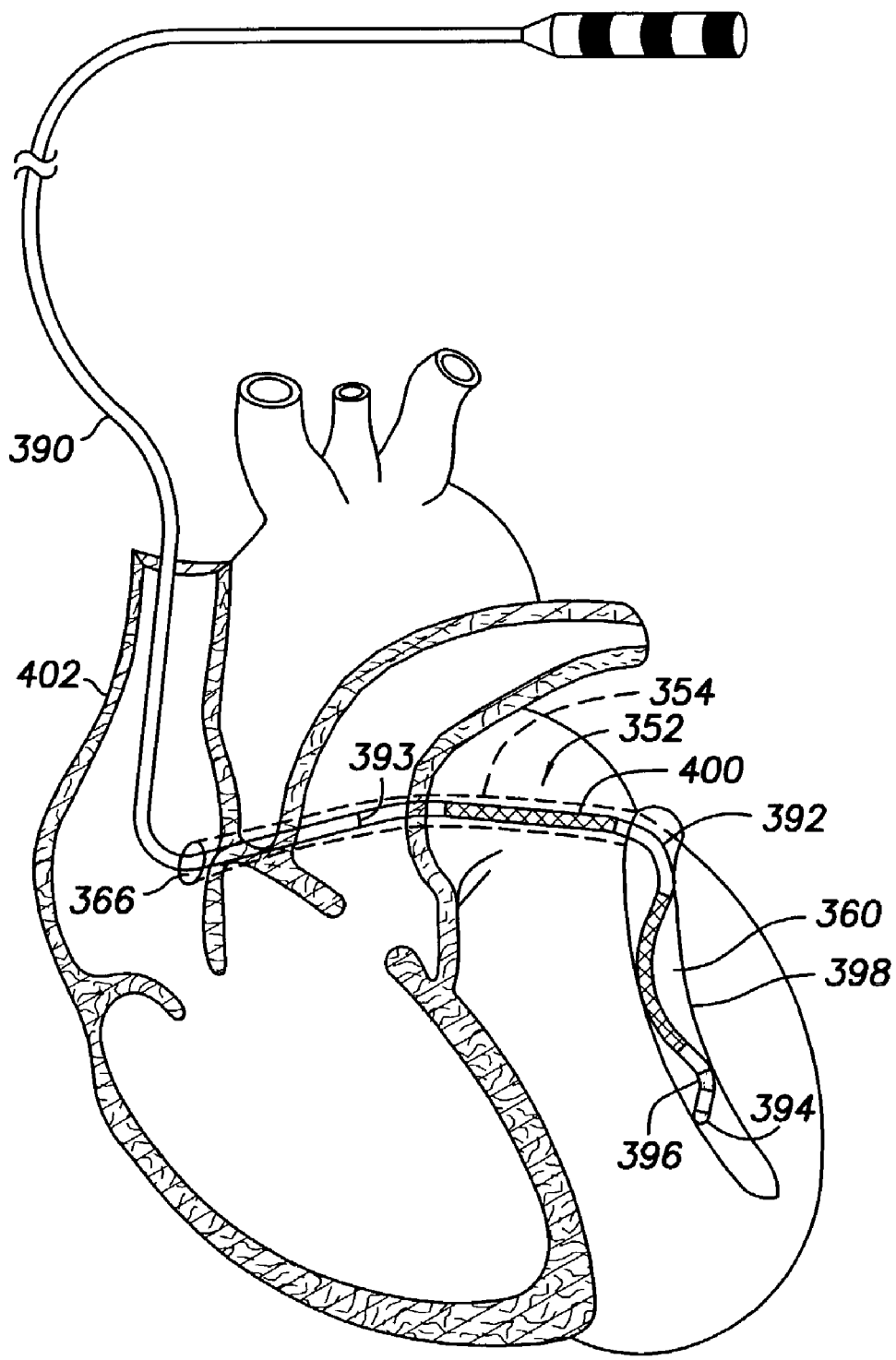
FIG. 16 is a perspective view of the anterior portion of the heart showing the distal portion of yet another lead body in accordance with the present invention implanted in the coronary sinus region thereof.

FIG. 16 shows a lead body 390 in accordance with yet another variation of the embodiment of FIG. 1 having a distal portion 392 implanted within the coronary sinus 354 and LPV vein 360 of the heart 350. The distal portion of the lead body extends distally from an interface 393 and carries a tip electrode 394, a ring sensing electrode 396, a distal cardioversion/defibrillation electrode 398 and a proximal cardioversion/defibrillation electrode 400. Here also, the interface joint at the stiffer proximal portion and the more flexible distal portion of the lead is distal to the coronary os. The tip electrode, the ring sensing electrode and the distal cardioversion/defibrillation electrode are shown residing in the LPV vein 360 while the proximal cardioversion/defibrillation electrode 400 is positioned in the distal portion of the coronary sinus 354.

FIGS. 14–16 show several examples of lead bodies in accordance with the present invention that may be implanted for left side stimulation and sensing. Other electrode combinations will be obvious to skilled artisans. For example, the proximal portions of the lead bodies shown in FIGS. 14–16 may be provided with a cardioversion/defibrillator electrode positioned to contact the wall of the right atrium and/or the SVC, identified by the reference numeral 402 in FIG. 16.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. An implantable stimulation lead comprising:
   at least one proximal connector;
   at least one tissue stimulation electrode;
   at least one conductor coupling the at least one proximal connector with the at least one stimulation electrode;
   a lead body of insulating material enclosing the at least one conductor, the lead body having a distal portion carrying the at least one tissue stimulation electrode, the lead body further having a proximal portion extending from the at least one proximal connector to a joint coupling the distal and proximal portions of the lead body, the joint comprising telescoped sections of the distal and proximal portions of the lead body, the telescoped sections of the distal and proximal portions of the lead body comprising a cored out section in one of the portions of the lead body and a reduced diameter section on the other of the portions of the lead body, the at least one conductor comprising a series combination of a first conductor within the proximal portion of the lead body and a second conductor within the distal portion of the lead body, a distal end of the first conductor being electrically connected within the joint to a proximal end of the second conductor, the cored out section of the distal portion of the lead body having a length greater than that of the reduced diameter section of the proximal portion of the lead body so as to define a space between distal ends of the reduced diameter and cored out sections, the space being filled with medical adhesive thereby isolating the proximal end of the second conductor from the proximal portion of the lead body.

2. The lead of claim 1 in which:
the second conductor is made of MP35N or MP35N/Ag and the proximal portion of the lead body is made of polyurethane.

3. The lead of claim 1 in which:
the cored out and reduced diameter sections are bonded to each other by medical adhesive.

4. The lead of claim 1 in which:
the cored out section having an inner diameter smaller than the outer diameter of the reduced diameter section whereby an interference fit exists between the cored out and reduced diameter sections.

5. The lead of claim 1 in which:
the at least one conductor comprises the series combination of a cable conductor and a coil conductor, the cable conductor having a proximal end electrically connected to the at least one proximal connector, the cable conductor having a distal end, the coil conductor having a distal end electrically connected to the at least one tissue stimulation electrode and a proximal end electrically connected to the distal end of the cable conductor.

6. The lead of claim 5 in which:
the joint includes a transition tube, the coil conductor having a proximal end including a plurality of windings disposed about the transition tube, the cable conductor having a distal end in electrical communication with the plurality of windings.

7. The lead of claim 6 in which:
the electrical communication between the distal end of the cable conductor and the plurality of windings at the proximal end of the coil conductor is effected by a crimp tube clamping the distal end of the cable conductor to the windings.

8. The lead of claim 6 in which:
the electrical communication between the distal end of the cable conductor and the plurality of windings at the proximal end of the coil conductor is effected by a weld.

9. The lead of claim 6 in which:
the transition tube has a distal part and a proximal part, the windings at the proximal end of the coil conductor being disposed about the distal part of the transition tube;
and which further includes:
a tubular liner of low friction material, the liner being disposed within a lumen in the proximal portion of the lead body, the liner having a distal end slipped over the proximal part of the transition tube.

10. The lead of claim 5 in which:
at least the proximal portion of the lead body comprises a multilumen housing, the cable conductor being contained within one of the lumens of the multilumen housing.

11. The lead of claim 10 in which:
the distal portion of the lead body comprises a multilumen housing, the coil conductor being contained within one of the lumens of the multilumen housing of the distal portion.

12. The lead of claim 10 in which:
a tubular liner of low friction material is contained within another one of the lumens of the multilumen lead body.

13. The lead of claim 12 in which:
the tubular liner comprises PTFE.

14. An implantable stimulation lead suitable for placement in the coronary sinus region and its associated coronary vessels overlying the left side of a patient's heart, the lead comprising:
at least one proximal connector;
at least one tissue stimulation electrode;
at least one conductor coupled between the at least one proximal connector and the at least one stimulation electrode;
a lead body of insulation material enclosing the at least one conductor, the lead body having a relatively flexible distal portion having a length corresponding to the coronary sinus region of the heart, the distal portion of the lead body carrying the at least one tissue stimulation electrode, the lead body further having a proximal portion that is stiffer than the distal portion and that extends from the at least one proximal connector to a joint coupling the distal and proximal portions of the lead body;
wherein the at least one conductor comprises a series combination of a cable conductor and a coil conductor, the cable conductor having a proximal end electrically connected to the at least one proximal connector, the cable conductor having a distal end, the coil conductor having a distal end electrically connected to the at least one tissue stimulation electrode and a proximal end electrically connected to the distal end of the cable conductor;
wherein the coil conductor is made of MP35N; and
a cored out section of the distal portion of the lead body having a length greater than that of a reduced diameter section of the proximal portion of the lead body so as to define a space between distal ends of the reduced diameter and cored out sections, the space being filled with medical adhesive thereby isolating the proximal end of the coil conductor from the proximal portion of the lead body.

15. The lead of claim 14 in which:
the joint comprises telescoped sections of the distal and proximal portions of the lead body.

16. The lead of claim 15 in which:
the telescoped section of the distal portion overlaps the telescoped section of the proximal portion of the lead body.

17. The lead defined in claim 15 in which:
the telescoped sections are bonded with a medical adhesive.

18. The lead of claim 14 in which:
the cored out section of the distal portion of the lead body has an inner diameter smaller than the outer diameter of the reduced diameter section of the proximal portion of the lead body whereby an interference fit exists between the cored out and reduced diameter sections.

19. The lead of claim 14 in which:
the cored out and reduced diameter sections are bonded to each other by medical adhesive.

20. The lead of claim 14 in which:
the joint includes a transition tube, the coil conductor having a proximal end including a plurality of windings disposed about the transition tube, the cable conductor having a distal end in electrical communication with the plurality of windings.

21. The lead of claim 20 in which:
the electrical communication between the distal end of the cable conductor and the plurality of windings at the proximal end of the coil conductor is effected by a crimp tube clamping the distal end of the cable conductor to the windings.

22. The lead of claim 20 in which:
the electrical communication between the distal end of the cable conductor and the plurality of windings at the proximal end of the coil conductor is effected by a weld.

23. The lead of claim 20 in which:
the transition tube has a distal part and a proximal part, the windings at the proximal end of the coil conductor being disposed about the distal part of the transition tube;
and which further includes:
a tubular liner of low friction material, the liner being disposed within a lumen in the proximal portion of the lead body, the liner having a distal end slipped over the proximal part of the transition tube.

24. The lead of claim 14 in which:
at least the proximal portion of the lead body comprises a multilumen housing, the cable conductor being contained within one of the lumens of the multilumen housing.

25. The lead of claim 24 in which:
the distal portion of the lead body comprises a multilumen housing, the coil conductor being contained within one of the lumens of the multilumen housing of the distal portion.

26. The lead of claim 24 in which:
a tubular liner of low friction material is contained within another one of the lumens of the multilumen lead body.

27. The lead of claim 26 in which:
the tubular liner is contained within the proximal portion of the lead body.

28. The lead of claim 26 in which:
the tubular liner is contained within both the proximal and distal portions of the lead body.

29. The lead of claim 26 in which:
the tubular liner, comprises PTFE.

30. The lead of claim 14 further comprising:
a stylet stop disposed within the distal portion of the lead body, the stylet stop defining an aperture dimensioned to pass a guide wire but not a distal tip of a stylet, and wherein the at least one stimulation electrode is a tip electrode, and the tip electrodes includes a longitudinally extending bore dimensioned to permit passage of the guide wire through the tip electrode.

31. The lead of claim 30 in which:
the stylet stop comprises a tubular member having an inner wall, the tubular member including an annular protuberance projecting inwardly from the inner wall of the tubular member, the annular protuberance defining the aperture, wherein a stylet, inserted in a lumen of the lead, is advanced within the lumen until an enlarged distal tip of the stylet engages the annular protuberance.

32. The lead of claim 30, wherein:
the at least one electrode further comprises a defibrillation electrode.

33. The lead of claim 32, wherein:
the defibrillation electrode is made of flexible material suitable for tracking the delivery means into a distal coronary vessel without stressing the vessel.

34. The lead of claim 33, wherein:
the defibrillation electrode is made of a conductive polymer.

35. The lead of claim 14, wherein:
the flexible distal portion of the lead body has an outer diameter smaller than that of the stiffer proximal portion so as to facilitate access to narrow, distal coronary vessels.

36. The lead of claim 14, wherein:
the flexible distal portion of the insulating lead body is made of silicone rubber.

37. The lead of claim 36, wherein:
the stiffer proximal portion of the insulating lead body is made of polyurethane.

38. An implantable stimulation lead suitable for placement in the coronary sinus region and its associated coronary vessels overlying the left side of a patient's heart, the lead comprising:
at least one proximal connector;
at least one tissue stimulation electrode;
at least one conductor coupled between the at least one proximal connector and the at least one stimulation electrode; and
a lead body comprising a housing of insulating material enclosing the at least one conductor, the lead body having a relatively flexible distal portion having a length corresponding to the coronary sinus region of the heart, the distal portion of the lead body carrying the at least one tissue stimulation electrode, the lead body further defining a proximal portion that is stiffer than the distal portion and that extends from the at least one proximal connector to a proximal portion/distal portion interface at the proximal extremity of the distal portion of the lead body, the distal portion of the lead body being configured to engage the wall of the coronary vessel in which the distal portion of the lead body is implanted to passively anchor the distal portion of the lead body in the coronary vessel;
wherein the at least one conductor comprises a series combination of a cable conductor and a coil conductor, the cable conductor having a proximal end electrically connected to the at least one proximal connector, the cable conductor having a distal end, the coil conductor having a distal end electrically connected to the at least one tissue stimulation electrode and a proximal end electrically connected to the distal end of the cable conductor; and
a cored out section of the distal portion of the lead body having a length greater than that of a reduced diameter section of the proximal portion of the lead body so as to define a space between distal ends of the reduced diameter and cored out sections, the space being filled with medical adhesive thereby isolating the proximal end of the coil conductor from the proximal portion of the lead body.

39. The lead of claim 38 in which:
the distal portion of the lead body is configured with at least one bend.

40. The lead of claim 39 in which:
the distal portion of the lead body is configured with at least one S-shaped bend.

41. The lead of claim 38 in which:
the distal portion of the lead body has an outer surface at least a portion of which surface is texturized to aid in passively anchoring the distal portion.

* * * * *